(12) United States Patent
Viola

(10) Patent No.: US 8,109,948 B2
(45) Date of Patent: Feb. 7, 2012

(54) COMPRESSION ANASTOMOSIS DEVICE AND METHOD

(75) Inventor: Frank J. Viola, Sandy Hook, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 990 days.

(21) Appl. No.: 11/827,691

(22) Filed: Jul. 13, 2007

(65) Prior Publication Data
US 2008/0004641 A1 Jan. 3, 2008

Related U.S. Application Data

(63) Continuation of application No. 11/243,636, filed on Oct. 5, 2005, now Pat. No. 7,285,125.

(60) Provisional application No. 60/620,021, filed on Oct. 18, 2004.

(51) Int. Cl.
A61B 17/08 (2006.01)
(52) U.S. Cl. ........................................................ 606/153
(58) Field of Classification Search .................. 606/158, 606/151–156
See application file for complete search history.

(56) References Cited

U.S. PATENT DOCUMENTS

| | | | |
|---|---|---|---|
| 3,254,650 A | 6/1966 | Collito | |
| 3,496,939 A | 2/1970 | Odiaga et al. | |
| 3,974,835 A | 8/1976 | Hardy, Jr. | |
| 4,055,186 A | 10/1977 | Leveen | |
| 4,154,241 A | 5/1979 | Rudie | |
| 4,182,339 A | 1/1980 | Hardy, Jr. | |
| 4,233,981 A | 11/1980 | Schomacher | |
| 4,294,255 A | 10/1981 | Geroc | |
| 4,467,804 A | 8/1984 | Hardy et al. | |
| 4,552,148 A | 11/1985 | Hardy, Jr. et al. | |
| 4,598,712 A | 7/1986 | Rebuffat et al. | |
| 4,633,873 A | 1/1987 | Dumican et al. | |
| 4,667,673 A | 5/1987 | Li | |
| 4,705,039 A | 11/1987 | Sakaguchi et al. | |
| 4,708,141 A | 11/1987 | Inoue et al. | |
| 4,766,898 A | 8/1988 | Hardy et al. | |
| 4,873,977 A | 10/1989 | Avant et al. | |
| 4,899,744 A | 2/1990 | Fujitsuka et al. | |
| 4,931,057 A | 6/1990 | Cummings et al. | |
| 4,964,863 A * | 10/1990 | Kanshin et al. | ............ 606/153 |

(Continued)

FOREIGN PATENT DOCUMENTS

EP 0119848 A2 9/1984

(Continued)

OTHER PUBLICATIONS

International Search Report for PCT/US06/10330 dated Jun. 13, 2008.

(Continued)

*Primary Examiner* — Gary Jackson
*Assistant Examiner* — Katherine Dowe

(57) ABSTRACT

An anastomotic device for use in the joining of a first tubular structure and a second tubular structure is provided. The anastomotic device includes a cylindrical sleeve configured and dimensioned for placement at least partially within the first tubular structure, the cylindrical sleeve defining a bore therethrough; an inverting member configured and dimensioned for placement at least partially within the second tubular structure, the inverting member defining a bore therethrough which is configured and dimensioned to selectively receive the cylindrical sleeve therein; and a constricting member selectively positionable on the inverting member and movable onto the cylindrical sleeve when the cylindrical sleeve is at least partially positioned within the bore of the inverting member.

9 Claims, 3 Drawing Sheets

U.S. PATENT DOCUMENTS

| | | | |
|---|---|---|---|
| 5,085,629 | A | 2/1992 | Goldberg et al. |
| 5,141,516 | A | 8/1992 | Detweiler |
| 5,156,623 | A | 10/1992 | Hakamatsuka et al. |
| 5,197,977 | A | 3/1993 | Hoffman, Jr. et al. |
| 5,222,963 | A | 6/1993 | Brinkerhoff et al. |
| 5,234,457 | A | 8/1993 | Andersen |
| 5,250,058 | A | 10/1993 | Miller et al. |
| 5,261,920 | A | 11/1993 | Main et al. |
| 5,282,810 | A | 2/1994 | Allen et al. |
| 5,289,831 | A | 3/1994 | Bosley |
| 5,290,271 | A | 3/1994 | Jemberg |
| 5,306,286 | A | 4/1994 | Stack et al. |
| 5,330,500 | A | 7/1994 | Song |
| 5,336,518 | A | 8/1994 | Narayanan et al. |
| 5,346,501 | A | 9/1994 | Regula et al. |
| 5,411,508 | A | 5/1995 | Bessler et al. |
| 5,425,738 | A | 6/1995 | Gustafson et al. |
| 5,464,415 | A | 11/1995 | Chen |
| 5,486,187 | A | 1/1996 | Schenick |
| 5,503,635 | A | 4/1996 | Sauer et al. |
| 5,549,122 | A | 8/1996 | Detweilwer |
| 5,609,629 | A | 3/1997 | Fearnot et al. |
| 5,618,298 | A | 4/1997 | Simon |
| 5,626,591 | A | 5/1997 | Kockerling et al. |
| 5,629,077 | A | 5/1997 | Turnlund et al. |
| 5,697,943 | A | 12/1997 | Sauer et al. |
| 5,766,710 | A | 6/1998 | Turnlund et al. |
| 6,068,636 | A | 5/2000 | Chen |
| 6,143,022 | A | 11/2000 | Shull et al. |
| 6,306,079 | B1 | 10/2001 | Trabucca |
| 6,379,379 | B1 | 4/2002 | Wang |
| 6,391,052 | B2 | 5/2002 | Buirge et al. |
| 6,488,701 | B1 | 12/2002 | Nolting et al. |
| 6,503,259 | B2 | 1/2003 | Huzel et al. |
| 6,537,310 | B1 | 3/2003 | Palmaz et al. |
| 6,569,173 | B1 | 5/2003 | Blatter et al. |
| 6,602,287 | B1 | 8/2003 | Millare et al. |
| 6,623,510 | B2 | 9/2003 | Belef et al. |
| 6,652,575 | B2 | 11/2003 | Wang |
| 6,666,873 | B1 | 12/2003 | Cassell |
| 6,736,824 | B2 | 5/2004 | Borghi |
| 6,736,825 | B2 | 5/2004 | Blatter et al. |
| 6,979,337 | B2 | 12/2005 | Kato |
| 7,059,510 | B2 | 6/2006 | Orban, III |
| 7,128,748 | B2 | 10/2006 | Mooradian et al. |
| 7,285,125 | B2 * | 10/2007 | Viola ............................ 606/153 |
| 2001/0034550 | A1 | 10/2001 | Buirge et al. |
| 2002/0011710 | A1 | 1/2002 | Oldenburg |
| 2002/0055769 | A1 | 5/2002 | Wang |
| 2002/0058955 | A1 | 5/2002 | Blatter et al. |
| 2002/0065527 | A1 | 5/2002 | Kato |
| 2002/0072694 | A1 | 6/2002 | Snitkin et al. |
| 2002/0082625 | A1 | 6/2002 | Huxel et al. |
| 2002/0099434 | A1 | 7/2002 | Buscemi et al. |
| 2002/0111590 | A1 | 8/2002 | Davila et al. |
| 2002/0133183 | A1 | 9/2002 | Lentz et al. |
| 2002/0188318 | A1 | 12/2002 | Carley et al. |
| 2002/0193864 | A1 | 12/2002 | Khosravi et al. |
| 2003/0028246 | A1 | 2/2003 | Palmaz et al. |
| 2003/0060877 | A1 | 3/2003 | Falotico et al. |
| 2003/0065346 | A1 | 4/2003 | Evens et al. |
| 2003/0069629 | A1 | 4/2003 | Jadhav et al. |
| 2003/0083614 | A1 | 5/2003 | Eisert |
| 2003/0114919 | A1 | 6/2003 | McQuiston et al. |
| 2003/0125799 | A1 | 7/2003 | Limon |
| 2003/0183671 | A1 | 10/2003 | Mooradian et al. |
| 2003/0216805 | A1 | 11/2003 | Edwin et al. |
| 2003/0225447 | A1 | 12/2003 | Majercak et al. |
| 2003/0236518 | A1 | 12/2003 | Marchitto et al. |
| 2004/0009289 | A1 | 1/2004 | Carley et al. |
| 2004/0073236 | A1 | 4/2004 | Carley et al. |
| 2004/0098119 | A1 | 5/2004 | Wang |
| 2004/0102758 | A1 | 5/2004 | Davila et al. |
| 2004/0116945 | A1 | 6/2004 | Sharkawy et al. |
| 2004/0116999 | A1 | 6/2004 | Ledgerber |
| 2004/0172048 | A1 | 9/2004 | Browning |
| 2006/0085060 | A1 | 4/2006 | Campbell |

FOREIGN PATENT DOCUMENTS

WO    WO2004/008937  A2    1/2004

OTHER PUBLICATIONS

European Search Report for EP 05807360.22310 date of completion is May 19, 2010 (3 pages).

International Search Report for PCT/US05/35699 date of completion is Apr. 6, 2007 (11 pages).

\* cited by examiner

COMPRESSION ANASTOMOSIS DEVICE AND METHOD

CROSS-REFERENCE TO RELATED APPLICATIONS

This application is a continuation of U.S. patent application Ser. No. 11/243,636, now U.S. Pat. No. 7,285,125 filed Oct. 5, 2005, which claims priority to U.S. Provisional Patent Application Ser. No. 60/620,021 filed Oct. 18, 2004, the disclosures of which are incorporated herein in their entirety by this reference.

BACKGROUND

1. Technical Field

The present disclosure generally relates to devices and methods for joining tubular structures via anastomosis. More particularly, the present disclosure relates to a compression anastomosis devices and methods of their use in surgical procedures.

2. Background of Related Art

Compression anastomotic devices have been developed in the past for receiving the free ends of anatomic tubular structures to be anastomosed. An example of such an anastomotic device has been developed by Tyco Healthcare LP, Norwalk, Conn., and is currently sold under the trademark VAL-TRAC®. This assembly includes a pair of ring members, each ring member for securement to the free end of each tubular structure to be anastomosed. Each ring member has a connecting structure, which mates with the other ring member to connect the ring members to one another. Reference may be made to U.S. Pat. No. 4,766,898 to Hardy et al., the contents of which are hereby incorporated by reference in their entirety, for a detailed discussion of the construction and operation of such an anastomotic device.

It is desirable in anastomotic surgery for a non-permanent connector or junction device to be used to join the ends of adjacent tubular structures since a permanent connector may prevent the changes in diameter necessary to facilitate the proper functioning of the tubular structure, e.g., a bowel or intestine. Accordingly, any foreign substances used in anastomotic surgery should partially or completely disintegrate, bio-absorb and/or bio-resorb once the tubular structures have partially or fully healed, desirably in a relatively short period of time.

The need exists for anastomotic devices which are simple to use, which meet the requirements of anastomotic surgery, and which are safe, and relatively inexpensive.

SUMMARY

According to an aspect of the present disclosure, an anastomotic device for use in the joining of a first tubular structure and a second tubular structure is provided. The anastomotic device includes a cylindrical sleeve configured and dimensioned for placement at least partially within the first tubular structure; an inverting member for facilitating positioning of at least a portion of the second tubular structure around at least a portion of the first tubular structure; and a constricting member supported on the inverting member and movable onto the cylindrical sleeve to constrict at least a portion of the second tubular structure towards at least a portion of the first tubular structure and towards the cylindrical sleeve.

The cylindrical sleeve defines a bore therethrough. It is envisioned that at least one of the cylindrical sleeve, the constricting member and the inverting member is bio-absorbable.

The cylindrical sleeve may include an inner diameter and an outer diameter. The outer diameter of the cylindrical sleeve is smaller than an inner diameter of the inverting member.

The constricting member may be a garter spring, which is configured to exert constrictive forces on at least a portion of the first tubular structure.

The anastomotic device may further include a rod which is configured and adapted for insertion through the first tubular structure and the second tubular structure. A portion of the first tubular structure may be sutured about the rod and a portion of the second tubular structure may also be sutured about the rod.

The rod includes a distal end having a dimension which is larger than the inner diameter of the cylindrical sleeve.

The anastomotic device further includes an ejecting member configured and adapted to move the constricting member from the inverting member to the cylindrical sleeve.

The anastomotic device further includes an ejecting member which facilitates positioning of the spring at least partially about the first tubular structure and the second tubular structure. The cylindrical sleeve includes a circumferential groove formed in an outer surface thereof for receiving the constricting member therein.

According to another aspect of the present disclosure, a method for joining a first tubular structure to a second tubular structure is provided. The method includes the steps of providing an anastomotic device having a cylindrical sleeve; an inverting member; a constricting member supported on the inverting member and movable onto the cylindrical sleeve; and a rod configured and adapted for insertion through the cylindrical sleeve, the inverting member, the first tubular structure and the second tubular structure.

The method further includes the steps of positioning the cylindrical sleeve onto a shaft portion of the rod; positioning the cylindrical sleeve, through the second tubular structure, into the first tubular structure; suturing a free end of the first tubular structure to the shaft portion of the rod; suturing a free end of the second tubular structure to the shaft portion of the rod; positioning the inverting member over the shaft portion of the rod and into the second tubular portion; and withdrawing the rod relative to the inverting member to approximate the cylindrical sleeve and the inverting member, such that at least a portion of second tubular structure is at least partially around the free end of the first tubular structure, creating a second tubular structure outer layer and an inner layer. The method further includes the step of moving the constricting member from the inverting member to the cylindrical sleeve such that the constricting member is positioned at least partially between the outer layer and the inner layer of the second tubular structure and outside of the first tubular structure, wherein the constricting member at least a portion of the first tubular structure and at least a portion of the second tubular structure towards the cylindrical sleeve.

The method may further include the step of cutting off at least a portion of the free end of the first tubular structure, at least a portion of the free end of the second tubular structure. The method may further include the step of allowing at least a portion of the first tubular structure and at least a portion of the second tubular structure to become joined with one another.

It is envisioned that the constricting member is a garter spring.

The method may further include the step of providing an ejecting member configured and adapted to facilitate positioning of the constricting member at least partially between the outer layer and the inner layer of the second tubular structure, and outside of the first tubular structure.

It is envisioned that at least one of the cylindrical sleeve, the inverting member and the constricting member is bio-absorbable.

According to yet another aspect of the present disclosure, an anastomotic device for use in the joining of a first tubular structure and a second tubular structure is provided. The anastomotic device includes a cylindrical sleeve configured and dimensioned for placement at least partially within the first tubular structure, the cylindrical sleeve defining a bore therethrough; an inverting member configured and dimensioned for placement at least partially within the second tubular structure, the inverting member defining a bore therethrough which is configured and dimensioned to selectively receive the cylindrical sleeve therein; and a constricting member selectively positionable on the inverting member and movable onto the cylindrical sleeve when the cylindrical sleeve is at least partially positioned within the bore of the inverting member.

The anastomotic device may further include an ejecting member configured and dimensioned to move the constricting member from the ejecting member to the cylindrical sleeve when the cylindrical sleeve is at least partially positioned within the bore of the inverting member.

The anastomotic device may still further include a rod selectively positionable through the bores of the cylindrical sleeve and the inverting member, wherein the rod includes a head portion configured and dimensioned to engage a distal-most end of the cylindrical sleeve and approximate the cylindrical sleeve toward the inverting member upon a proximal displacement of the rod relative to the inverting member.

It is envisioned that at least one of the cylindrical sleeve, the inverting member and the constricting member is bio-absorbable.

BRIEF DESCRIPTION OF THE DRAWINGS

Embodiments of the present disclosure are described hereinbelow with reference to the drawings wherein.

DETAILED DESCRIPTION

Figure 1:
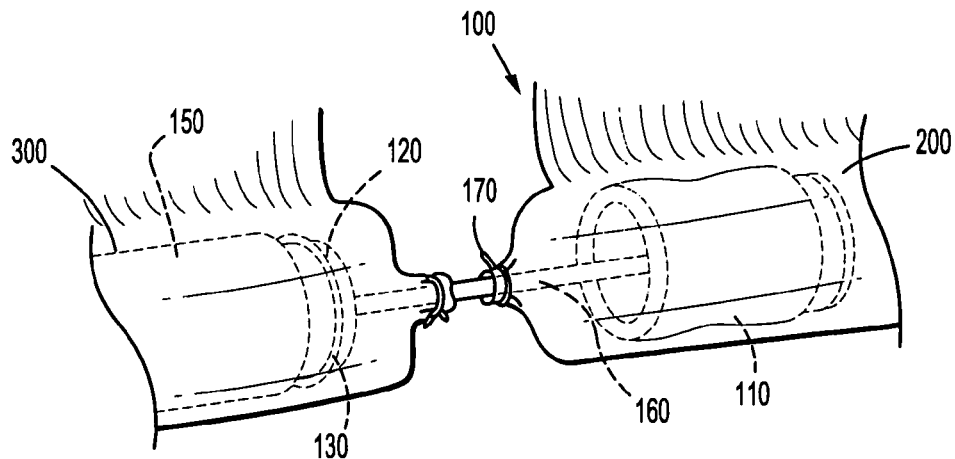
FIG. 1 is a perspective view of an anastomotic device of the present disclosure, illustrated partially within a first tubular structure and partially within a second tubular structure.

Embodiments of the presently disclosed compression anastomotic device and method will now be described in detail with reference to the drawing figures wherein like reference numerals identify similar or identical elements. As used herein and as is traditional, the term "distal" refers to that portion which is farthest from the user (generally illustrated on the figures as being towards the right) while the term "proximal" refers to that portion which is closest to the user (generally illustrated on the figures as being towards the left).

Figure 2:
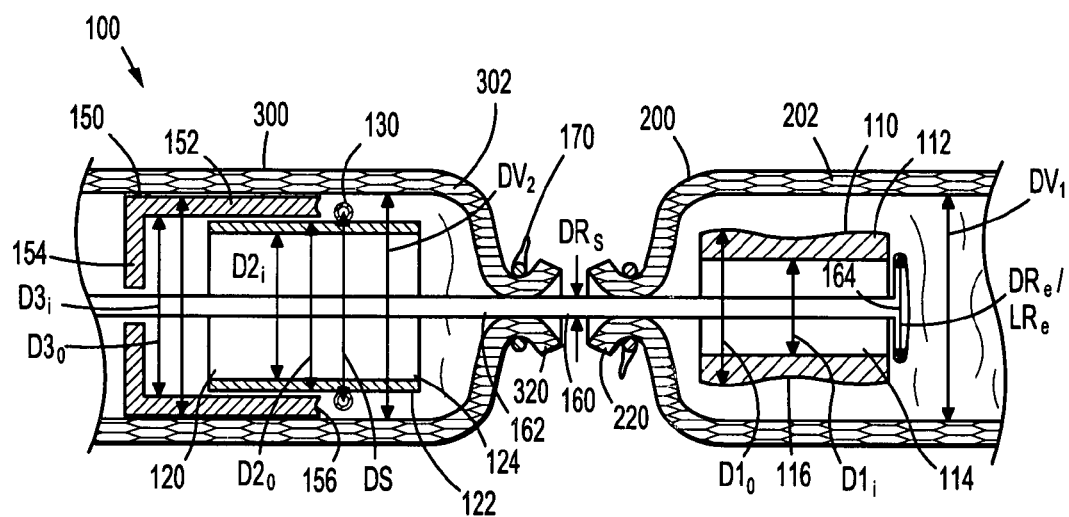
FIG. 2 is a longitudinal cross-sectional view of the anastomotic device and tubular structures of FIG. 1.

In accordance with the present disclosure, an anastomotic device 100 for joining a first tubular structure 200 and a second tubular structure 300, via anastomotic surgery, is provided. As shown in FIGS. 1 and 2, anastomotic device 100 generally includes a sleeve 110, an inverting member 120, and a constricting member, such as a spring, 130. With continued reference to FIGS. 1 and 2, anastomotic device 100 further includes an ejecting member 150 and an approximating rod member 160.

As shown in FIGS. 1-6, the sleeve 110 is generally cylindrical in shape; however, any other shape is envisioned, such as, for example, ovular, rectangular, etc. Cylindrical sleeve 110 includes an outer wall 112 defining a bore 114 therethrough. The cylindrical sleeve 110 has a maximum outer diameter $D1_o$ and an inner diameter $D1_i$. In an exemplary embodiment, the outer wall 112 of the cylindrical sleeve 110 includes a groove or depression 116 formed thereon. As will be described in greater detail below, cylindrical sleeve 110 is initially positioned at least partially within the first tubular structure 200. Desirably, cylindrical sleeve 110 is positioned entirely within first tubular structure 200.

As seen in FIGS. 1 and 2, inverting member 120 is configured and dimensioned to cooperate with sleeve 110. Accordingly, inverting member 120 desirably has a cylindrical shape. With continued reference to FIGS. 1 and 2, inverting member 120 includes an outer wall 122 defining a bore therethrough 124. The inverting member 120 has an outer diameter $D2_o$ and a minimum inner diameter $D2_i$. In an exemplary embodiment, the outer diameter $D1_o$ of the cylindrical sleeve 110 is smaller than the inner diameter $D2_i$ of the inverting member 120. As will be described in greater detail below, inverting member 120 is initially positioned at least partially within the second tubular structure 300. Desirably, inverting member 120 is positioned entirely within second tubular structure 300.

As seen in FIG. 1, the constricting member 130 is generally ring-like and is positionable around outer wall 122 of inverting member 120. When constricting member 130 is positioned about outer wall 122 of inverting member 120, constricting member 130 is in a biased condition (e.g., radially expanded condition) in which constricting member 130 exerts compressive forces on and/or about outer wall 122 of inverting member 120 (i.e., radially inward directed constricting forces). An exemplary constricting member 130 may take the form of a garter spring or the like. When positioned on outer wall 122 of inverting member 120, the constricting member 130 has an inner diameter DS which is equal to outer diameter $D2_o$ of outer wall 122 of inverting member 120.

With continued reference to FIGS. 1 and 2, ejecting member 150 includes an outer wall 152 having an outer diameter $D3_o$ and a minimum inner diameter $D3_i$. The inner diameter $D3_i$ of outer wall 152 is larger than the outer diameter $D2_o$ of outer wall 122 of inverting member 120. The outer diameter $D3_o$ is smaller than a diameter DV2 of the second tubular structure 300.

The ejecting member 150 further includes a proximal surface 154 through which shaft 162 of approximating rod 160 extends. In an exemplary embodiment, a distal-most surface 156 of outer wall 152 is arcuate and/or concave to engage and/or mate with constricting member 130.

As mentioned above, anastomotic device 100 further includes an approximating rod 160, as illustrated in FIGS. 1 and 2. Rod 160 includes a shaft portion 162 and a distal end portion 164. The shaft portion 162 has a diameter $DR_s$ which is smaller than the inner diameter $D1_i$ of outer wall 112 of cylindrical sleeve 110. Distal end portion 164 of rod 160 has a diameter $DR_e$ (or length $LR_e$) which is greater than the inner diameter $D1_i$ of outer wall 112 of cylindrical sleeve 110. The rod 160 may be initially positioned such that the distal end portion 164 is disposed distal of the cylindrical sleeve 110. The shaft portion 162 of the rod 160 may extend through the bore 114 of the outer wall 112 of cylindrical sleeve 110, through the bore 124 of the outer wall 122 of inverting member 120, and optionally through the proximal surface 154 of the ejecting member 150.

It is envisioned for at least the cylindrical sleeve 110, the inverting member 120, and the ejecting member 150 of the anastomotic device 100 to be constructed of a bio-absorbable material. Such components of anastomotic device 100 may be constructed from bio-absorbable polymeric resin such as, for example, a copolymer of polylactic acid (PLA) and polyglycolic acid (PGA). The relative proportion of the components may be chosen to suit the surgical application. For example, under identical processing conditions, PGA is typically the stronger of the two components and more crystalline. However, PGA is more rapidly absorbed by body tissue. Hence, for surgical applications where it is desired to maintain the implant strength over a longer period of time, the fiber will typically contain more PLA. The fibers can be fibers of the type used in manufacturing suture material. Additionally, several other materials for forming at least one component of the anastomotic device 100 are disclosed in U.S. Pat. No. 3,297,033 and are referred to as poly-hydroxyacetic ester and lactide co-polymers, the entire contents of which are incorporated by reference herein. The materials disclosed in the above-referenced patent constitute a partial list of possible materials as molded surgical articles made from a wide range of glycolide/lactide copolymers have been known and utilized for many years.

With reference to FIGS. 2-6, a method of using anastomotic device 100 in a surgical procedure will now be described in detail. Initially referring to FIG. 2, with the cylindrical sleeve 110 positioned on shaft portion 162 of approximating rod 160, cylindrical sleeve 110 and distal end portion 164 of approximating rod 160 are advanced through the lumen of second tubular structure 300 and positioned within the lumen of the first tubular structure 200, using known surgical techniques. Thereafter, a free end 220 of first tubular structure 200 is purse string sutured around shaft portion 162 of approximating rod 160 using a suture 170. In addition, a free end 320 of second tubular structure 300 is purse string sutured around shaft portion 162 of approximating rod 160 using a suture 170.

The inverting member 120 is then slid over shaft portion 162 of approximating rod 160 and distally through the lumen of the second tubular structure 300. Desirably, as seen in FIG. 2, the constricting member 130 is positioned around the outer wall 122 of the inverting member 120 prior to the positioning of the inverting member 120 within the lumen of the second tubular structure 300. With the inverting member 120 so positioned, ejecting member 150 is positioned over a proximal end of the shaft portion 162 of the approximating rod 160 and advanced distally into the lumen of the second tubular structure 300 until outer wall 152 of ejecting member 150 is disposed about the outer wall 122 of the inverting member 120.

Figure 3:
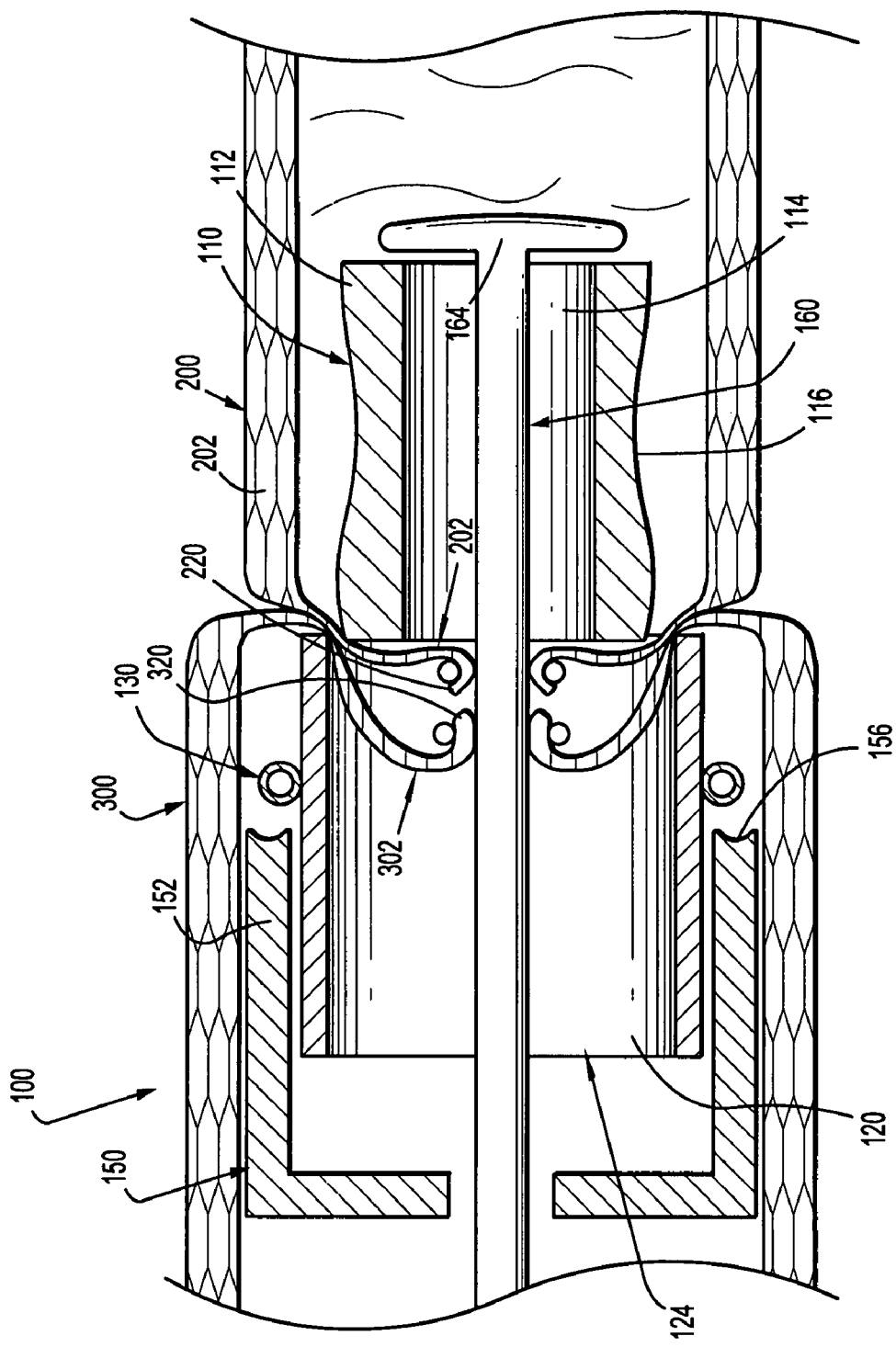
FIG. 3 is a longitudinal cross-sectional view of the anastomotic device and tubular structures of FIGS. 1 and 2, illustrating the first tubular structure partially positioned within a portion of the second tubular structure.
Figure 4:
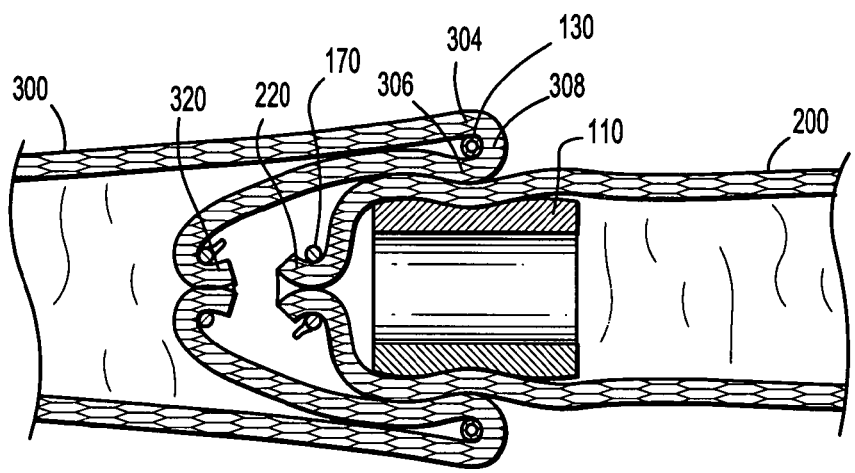
FIG. 4 is a longitudinal cross-sectional view of the anastomotic device and tubular structures of FIGS. 1-3, illustrating the first tubular structure partially positioned within the second tubular structure in accordance with the present disclosure.

To join the first tubular structure 200 with the second tubular structure 300, the rod 160 is pulled proximally relative to inverting member 120 to approximate first tubular structure 200 and second tubular structure 300. Since distal end portion 164 is larger than bore 114 of sleeve 110, proximal movement of the rod 160 pulls cylindrical sleeve 110 towards second tubular structure 300. Continued proximal movement of rod 160 causes the now sutured free end 220 of first tubular structure 200 to contact the now sutured free end 320 of second tubular structure 300 and to push free end 320 of second tubular structure 300 into bore 124 of inverting member 120, as illustrated in FIG. 3. In so doing, as seen in FIG. 4, an outer layer 304 and an inner layer 306 of second tubular structure 300 is created. Here, a portion 302 of second tubular structure 300 is positioned around a portion 202 of first tubular structure 200. As mentioned above, continued proximal movement of the rod 160 and cylindrical sleeve 110 pushes the free end 320 of the second tubular structure 300 within the bore 124 of the inversion structure 120, thus inverting the free end 320 of the second tubular structure 300, as illustrated in FIG. 4.

Once the free end 320 of the second tubular structure 300 is inverted, such that a proximal end portion of sleeve 110 is positioned within a distal end portion of bore 124 of inverting member 120, ejecting member 150 is advanced distally relative to inverting member 120. Ejecting member 150 is advanced distally an amount sufficient to push constricting member 130 off the distal end of inverting member 120 and onto the proximal end of sleeve 110 thereby constricting first and second tubular structures 200 and 300 onto sleeve 110. Desirably, constricting member 130 settles into groove 116 of cylindrical sleeve 110 and defines a fold 308 in second tubular structure 300.

As seen in FIG. 4, the constricting forces exerted by the constricting member 130 maintain its location within groove 116 and adjacent the fold 308. The constricting member 130 compresses, constricts or pinches a portion of the second tubular structure 300 and a portion of the first tubular structure 200 about cylindrical sleeve 110.

In accordance with a method of the present disclosure, rod 160 may be removed by breaking and/or cutting shaft portion 162 along the length thereof or, in the alternative, by separating the head portion 164 from shaft portion 162 using any known surgical technique. In another method, head portion 164 may be fabricated from a substantially rigid, pliable or deflectable material. In this manner, as rod 160 is drawn in a proximal direction relative to cylindrical sleeve 110, head portion 164 will be sufficiently rigid to approximate first and second tubular structures 200 and 300 and be sufficiently pliable in order to deflect or flex an amount sufficient to enter and pass through the bore 114 of cylindrical sleeve 110.

Figure 5:
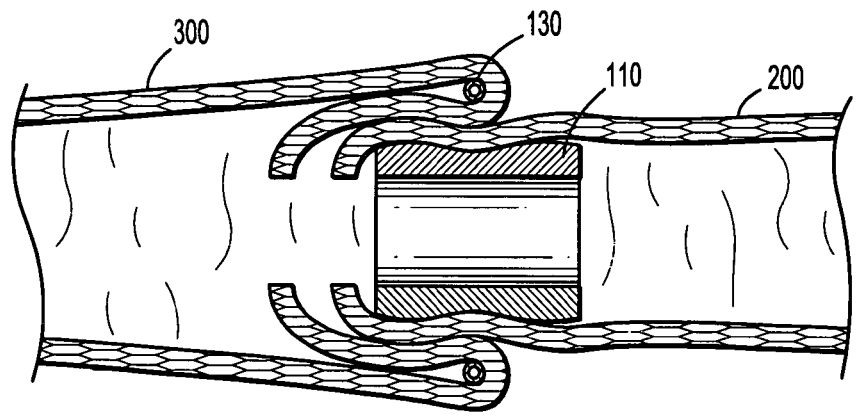
FIG. 5 is a longitudinal cross-sectional view of the anastomotic device and tubular structures of FIGS. 1-4, illustrating the purse-stringed portions of each of the first tubular structure and second tubular structure having been cut off.

As seen in FIG. 5, suture 170 and the free ends 220, 320 of the first and second tubular structures 200, 300, respectively, have been surgically removed or excised, using known surgical techniques. As can be appreciated, bodily fluids and the like can now pass from the first tubular structure 200 to the second tubular structure 300, or vice versa.

Figure 6:
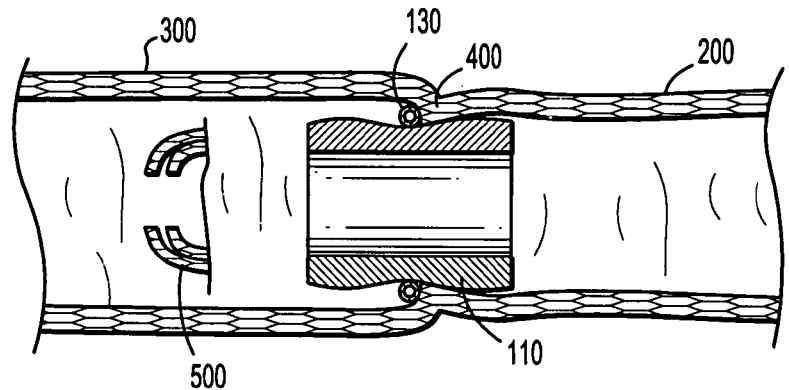
FIG. 6 is a longitudinal cross-sectional view of the anastomotic device and tubular structures of FIGS. 1-5, illustrating separation of necrosed rings of tissue from the anastomosed tubular structure.

As seen in FIG. 6, constricting member 130 radially constricts first and second tubular structures 200 and 300 about sleeve 110 thereby constricting blood flow to portions 202 and 302 of first and second tubular structures thereby causing portions 202 and 302 to necrose and eventually separate from the remainder of first and second tubular portions 200 and 300. Meanwhile, the compression by the constricting member 130 results in the tubular structures 200, 300 anastomosing or fusing with one another to form a joined tissue 400.

As seen in FIG. 6, once dead tissue 500 loses its physical strength and breaks off from the living portions of the tissue 202, 302, dead tissue 500 harmlessly passes out of the body. At this point, cylindrical sleeve 110 and the constricting member 130 will detach from the tubular structures 200, 300 and pass through the body or, alternatively, cylindrical sleeve 110 and constricting member 130 may be absorbed by the body, if fabricated from bio-absorbable materials.

Once healing is complete, the two tubular structures 200, 300 will have been joined together and have produced a continuous and strong lumen.

While the above description contains many specifics, these specifics should not be construed as limitations on the scope of the present disclosure, but merely as exemplifications of various embodiments thereof. Those skilled in the art will envision many other possible variations that are within the scope and spirit of the present disclosure.

What is claimed is:

1. A method of joining a first tubular structure and a second tubular structure, comprising:
    providing an anastomosis device comprising a first sleeve and a second sleeve;
    placing the first sleeve within the first tubular structure;
    placing the second sleeve within the second tubular structure;
    positioning at least one of the first sleeve and the second sleeve onto a rod;
    suturing a portion of the first tubular structure and a portion of the second tubular structure onto a portion of the rod;
    positioning the second sleeve around the first sleeve so that an end of the first tubular structure is positioned around at least a portion of the first sleeve and an end of the second tubular structure is positioned around the end of the first tubular structure;
    removing the second sleeve from within the second tubular structure;
    withdrawing the rod such that the portions of the tubular structures that have been sutured are positioned laterally spaced from the first sleeve, and wherein the first sleeve is the only portion of the anastomosis device that remains within at least one of the first and the second tubular structures.

2. The method according to claim 1, further comprising moving a constricting member from a position on the second sleeve to a position on the first sleeve.

3. The method according to claim 2, wherein the constricting member is positioned around the end of the second tubular structure.

4. The method according to claim 1, wherein the second sleeve is positioned around the first sleeve by engaging the first sleeve with the rod.

5. The method according to claim 4, wherein the rod is moved in a direction toward the second sleeve.

6. The method according to claim 5, wherein the first sleeve is inserted in the second sleeve.

7. The method according to claim 2, wherein the constricting member is moved in a direction toward the first sleeve by an ejecting member.

8. The method according to claim 7, wherein the ejecting member is disposed around the second sleeve.

9. The method according to claim 2, wherein the constricting member is moved into a groove formed in the outer surface of the first sleeve.

\* \* \* \* \*